US006418791B1

United States Patent
Lanni et al.

(10) Patent No.: US 6,418,791 B1
(45) Date of Patent: Jul. 16, 2002

(54) SYSTEM AND METHOD FOR ACOUSTIC INTEGRITY MONITORING

(75) Inventors: Arthur L. Lanni, Cary; Mietek T. Glinkowski, Raleigh, both of NC (US)

(73) Assignee: ABB Technology AG, Zurich (CH)

( * ) Notice: Subject to any disclaimer, the term of this patent is extended or adjusted under 35 U.S.C. 154(b) by 0 days.

(21) Appl. No.: 09/532,655

(22) Filed: Mar. 22, 2000

(51) Int. Cl.7 .............................................. G01N 29/10
(52) U.S. Cl. .............................. 73/602; 73/614; 73/629
(58) Field of Search ........................ 73/597, 598, 599, 73/600, 602, 627, 628, 629, 610, 614

(56) References Cited

U.S. PATENT DOCUMENTS

| | | | |
|---|---|---|---|
| 3,583,213 A | 6/1971 | Houck | 73/67.5 |
| 4,103,291 A | 7/1978 | Howe et al. | 340/522 |
| 4,223,790 A | 9/1980 | Yoshida | 209/590 |
| 4,320,659 A | 3/1982 | Lynnworth et al. | 73/589 |
| 4,402,224 A | 9/1983 | Fukushima | 73/705 |
| 4,547,769 A | 10/1985 | Tanigaki et al. | 340/626 |
| 4,574,615 A | 3/1986 | Bower et al. | 73/24 |
| 4,635,042 A | 1/1987 | Andrews | 340/605 |
| 4,738,137 A | 4/1988 | Sugg et al. | 73/587 |
| 4,937,698 A | 6/1990 | Toya et al. | 361/86 |
| 5,392,635 A | 2/1995 | Cadel et al. | 73/24.01 |
| 5,501,098 A | 3/1996 | Cadel et al. | 73/24.01 |
| 5,542,298 A | 8/1996 | Sarvasian et al. | 73/597 |
| 5,625,140 A | 4/1997 | Cadet et al. | 73/24.01 |
| 5,675,074 A | 10/1997 | Melvin, II | 73/52 |
| 5,693,881 A | 12/1997 | Sitachitt et al. | 73/290 |
| 5,739,418 A | 4/1998 | Hackel et al. | 73/35.11 |
| 5,739,419 A | 4/1998 | Maier et al. | 73/37 |

FOREIGN PATENT DOCUMENTS

| | | | |
|---|---|---|---|
| DE | 195 26 394 A1 | 1/1997 | |
| DE | 195 39 535 A1 | 4/1997 | |
| DE | 19539535 A1 * | 4/1997 | 73/597 |
| GB | 2 253 698 A * | 9/1992 | 73/597 |

* cited by examiner

Primary Examiner—Hezron Williams
Assistant Examiner—Rose M. Miller
(74) Attorney, Agent, or Firm—Woodcock Washburn LLP (57) ABSTRACT

A method and system are disclosed for monitoring vacuum integrity in a vacuum interrupter. The method includes injecting sonic signals into a body and detecting sonic signals reflected from the body. A composite value is calculated from the reflected sonic signals and a determination made based on the composite value as to whether the vacuum is acceptable. The system includes the following components: a transducer for sending sonic signals into a body; a receiver for receiving sonic signals reflected from the body; a signal processor for calculating a composite value from the sonic signals reflected from the body; and a processing unit for determining from the composite value whether the body has an acceptable vacuum therein.

23 Claims, 7 Drawing Sheets

SYSTEM AND METHOD FOR ACOUSTIC INTEGRITY MONITORING

FIELD OF THE INVENTION

This invention relates generally to vacuum measurements, and more particularly to systems and methods for monitoring the integrity of a vacuum interrupter.

BACKGROUND OF THE INVENTION

Generally, the operation of a vacuum interrupter for use with an electric power circuit deteriorates as the vacuum in the interrupter deteriorates, i.e. the pressure in the interrupter increases. When the vacuum deteriorates, the small contact spacing upon which operation of the interrupter depends, can no longer sustain the high voltage applied to the contacts. As a result, arcs and flash-overs are likely to occur, causing damage to the interrupter. Pressure within a vacuum interrupter may increase because of, for example, outgassing from materials used for the interrupter or leakage of air into the interrupter.

In order to avoid the problems associated with loss of vacuum, it has been recognized that vacuum interrupters ought to be monitored for vacuum integrity. A simple, accurate, and non-intrusive system for performing this monitoring, however, has not been developed. There is a need, therefore, for an improved system and method for monitoring the integrity of vacuum interrupters. In particular, there is a need for a method and system for acoustic sensing of vacuum integrity.

SUMMARY OF THE INVENTION

Briefly, the present invention provides systems and methods for acoustic sensing of vacuum integrity. According to one aspect of the invention, there is provided a method for vacuum integrity sensing, comprising the following steps: injecting sonic signals into the body; detecting sonic signals reflected from the body; calculating a composite value from the sonic signals reflected from the body; and determining using said composite value if the body has an acceptable vacuum therein.

According to another aspect of the invention, there is provided a system for acoustic sensing of vacuum integrity comprising the following components: a transducer for sending sonic signals into a body; a receiver for receiving sonic signals reflected from the body; a signal processor for calculating a composite value from the sonic signals reflected from the body; and a processing unit for determining from said composite value whether the body has an acceptable vacuum therein.

The above-listed features of the present invention will be more fully set forth hereinafter.

BRIEF DESCRIPTION OF THE DRAWINGS

Other features of the invention are further apparent from the following detailed description of the presently preferred exemplary embodiments of the invention taken in conjunction with the accompanying drawings, of which.

DETAILED DESCRIPTION OF PREFERRED EMBODIMENT

Generally, sonic waves, especially ultrasonic waves travel through solid, liquid, and gaseous media but do not travel through a vacuum. This characteristic provides the basis for a non-intrusive method of monitoring the integrity of a vacuum interrupter.

Figure 1A:
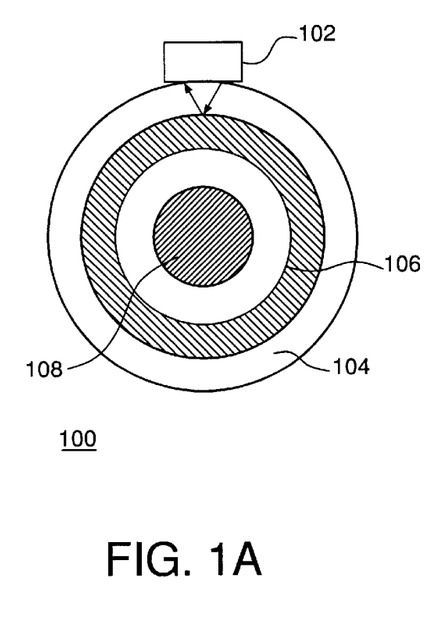
FIGS. 1A and 1B provide sectional views of a vacuum interrupter.
Figure 1B:
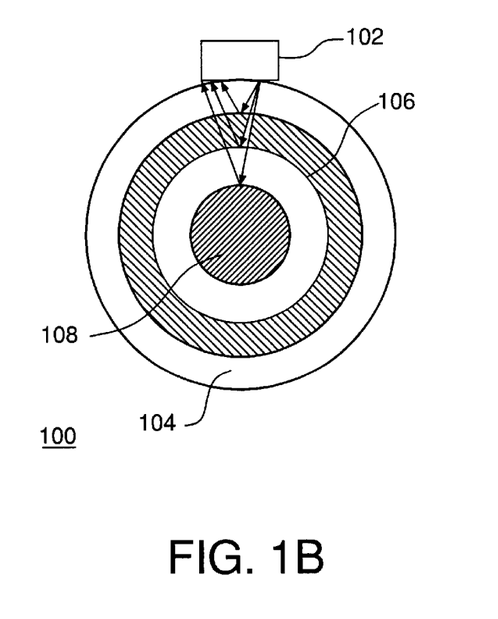

FIGS. 1A and 1B are sectional views of vacuum interrupter 100 with attached sound transducer 102. Vacuum interrupter 100 comprises envelope 104, vapor shield 106, and contacts 108.

FIG. 1A depicts a situation wherein an ideal vacuum exists between envelope 104 and contacts 108. Ultrasonic signals, depicted by arrows 110, which are directed into the interrupter 100 reflect off of the inner wall of the envelope 104. However, because a vacuum exists within, the signals do not have a medium through which to propagate and therefore cannot penetrate further into interrupter 100.

In contrast, FIG. 1B depicts a situation wherein the vacuum within interrupter 100 has deteriorated. As shown, ultrasonic signals 110 penetrate within vacuum interrupter 100 and are reflected off of vapor shield 106 and contacts 108. The signals are able to penetrate into interrupter 100 because the vacuum therein is imperfect and the sonic waves have a medium through which to propagate. As a consequence, a composite signal reflected from interrupter 100 over a prescribed period of time will be larger in comparison to an intact vacuum due to the increased number of reflections associated with a deteriorated vacuum.

Applicants have determined that it is possible to use the signals reflected out of the interrupter to distinguish between the situation depicted in FIG. 1A where the vacuum is intact and the situation depicted in FIG. 1B where the vacuum has deteriorated. Specifically, if a composite of the reflected signals detected over a prescribed period of time exceed a predetermined value, the vacuum can be identified as having deteriorated.

Figure 2:
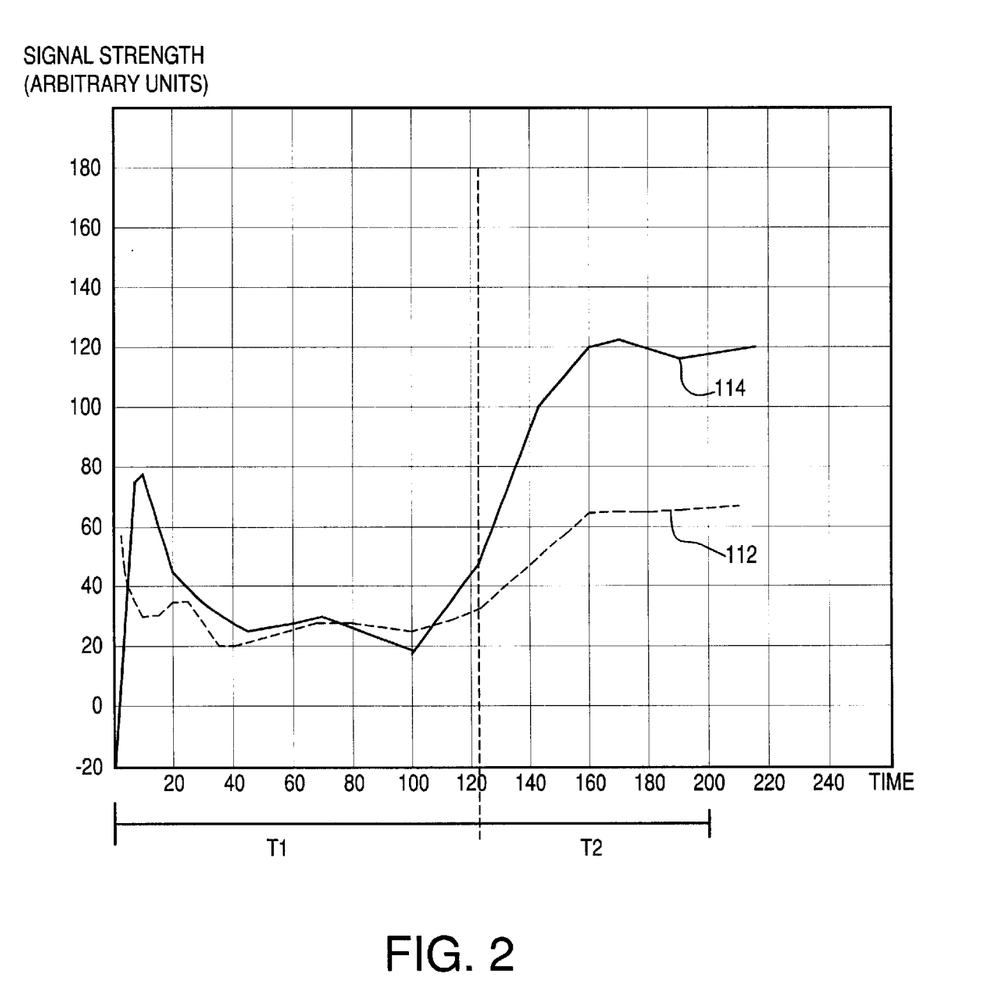
FIG. 2 is a line graph of ultrasonic signal reflected from a vacuum interrupter.

FIG. 2 illustrates the marked difference in sonic signals reflected from vacuum interrupter 1A in which the vacuum is intact and FIG. 1B in which the vacuum has deteriorated. Dashed line 112 corresponds to the signal reflected from interrupter 100 in FIG. 1A. Solid line 114 corresponds to the signal reflected from interrupter 100 in FIG. 1B. During time period T1, which represents the period of time in which signals are reflected from the inner wall of envelop 104, the difference between signals 112 and 114 is not greatly pronounced. However, after time period T1 and during time period T2, signal 114 becomes significantly greater than signal 112. Accordingly, it is possible, especially during time period T2, to discern whether a vacuum is intact based upon the strength of a signal reflected from the interrupter.

Figure 3:
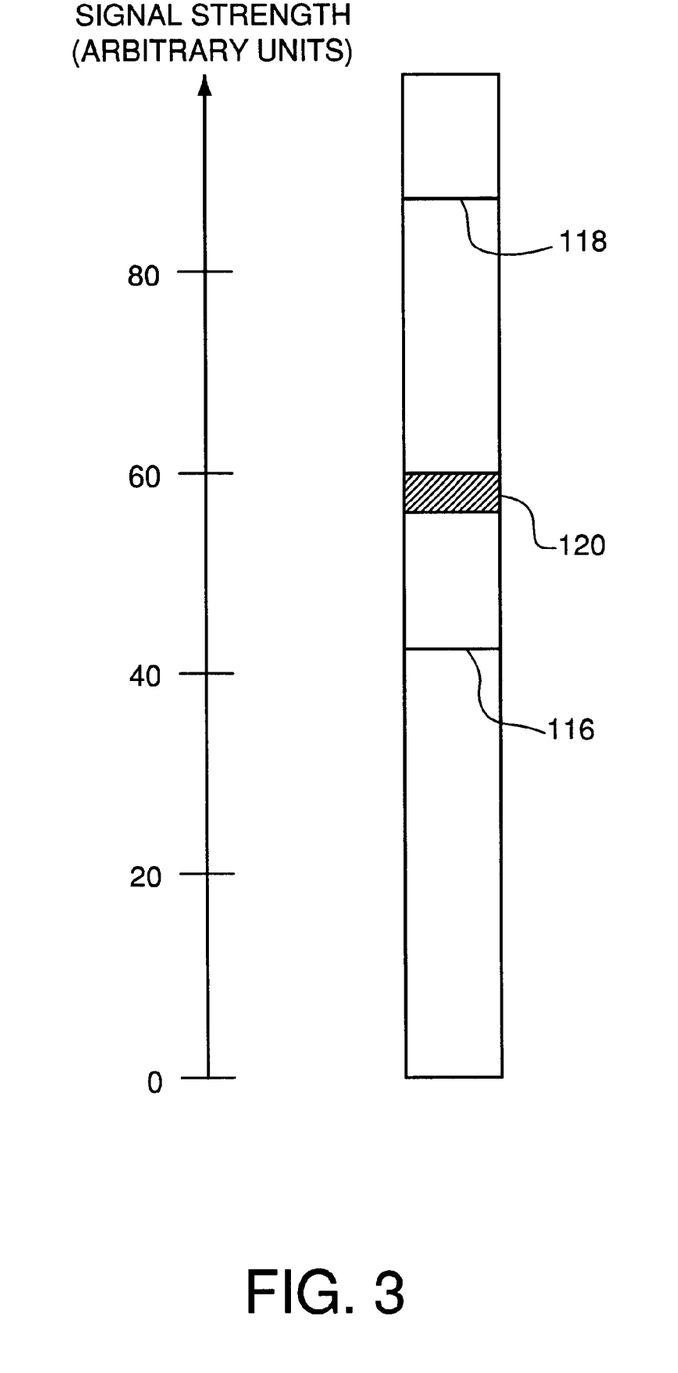
FIG. 3 is a bar graph depicting acceptable and unacceptable ultrasonic signal strength reflected from a vacuum interrupter.

FIG. 3 is a bar chart of composite values of reflected signals. The signal value corresponding to a vacuum interrupter with a vacuum intact is represented by line 116. The signal value corresponding to an interrupter with a deteriorated vacuum is represented by line 118. As shown, line 118 is significantly higher than line 116. Accordingly, it is possible using the value of a reflected signal to delineate between interrupters with intact and deteriorated vacuums. Area 120 represents a range of values for which the signal is not ideal but is nonetheless acceptable.

Figure 4:
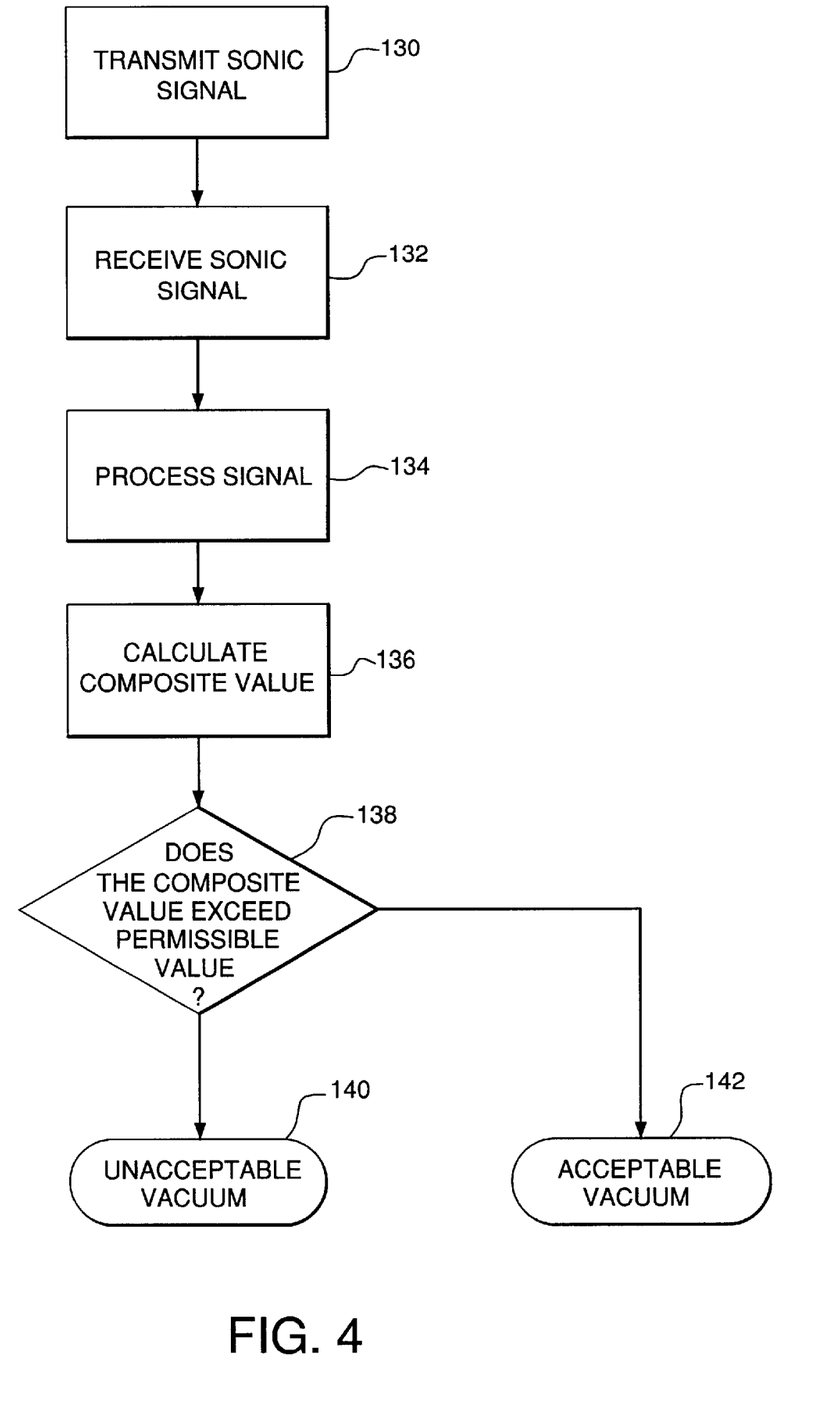
FIG. 4 is a flow chart of a method for monitoring the integrity of a vacuum in accordance with the present invention.

FIG. 4 is a flow chart of a method based upon the above described principles for acoustic monitoring of vacuum integrity in a vacuum interrupter. As shown, at step 130, a sonic signal is transmitted into the vacuum interrupter. At step 132, the sonic signal reflected from the vacuum interrupter is received. It might be necessary, as depicted by step 134, to perform signal processing on the signal received at step 132 in order to prepare the signal for further consideration. For example, with respect to the signals depicted in FIG. 2, it might be useful to filter the signal received during time T1 so that only those values received during time T2, i.e. those that are more clearly definitive, are considered. At step 136, a composite value is calculated from the signal processed at step 134. The composite value may be an average, a mean, or other function representative of the reflected sonic signal. At step 138, it is determined whether the composite value exceeds a predetermined permissible value. If the composite value exceeds the permissible value, at step 140, it is determined that the vacuum has reached an unacceptable level. Of course, if the composite does not exceed the permissible value, at step 142, it is determined that the vacuum is acceptable.

It should be noted that the predetermined permissible value referred to at step 138 may be derived in any number of different ways. For example, a reflected signal value corresponding to an acceptable vacuum may be determined through testing for a given make and model of vacuum interrupter. This value can be used as the predetermined permissible value for evaluating other vacuum interrupters of the same make and model. A predetermined permissible value might also be derived for a specific vacuum interrupter. For example, when a vacuum interrupter is first installed, a reflected signal value might be measured and saved. Reflected signal value measurements made thereafter for the same vacuum interrupter can be compared to this saved value and an evaluation made as to vacuum degradation.

Figure 5:
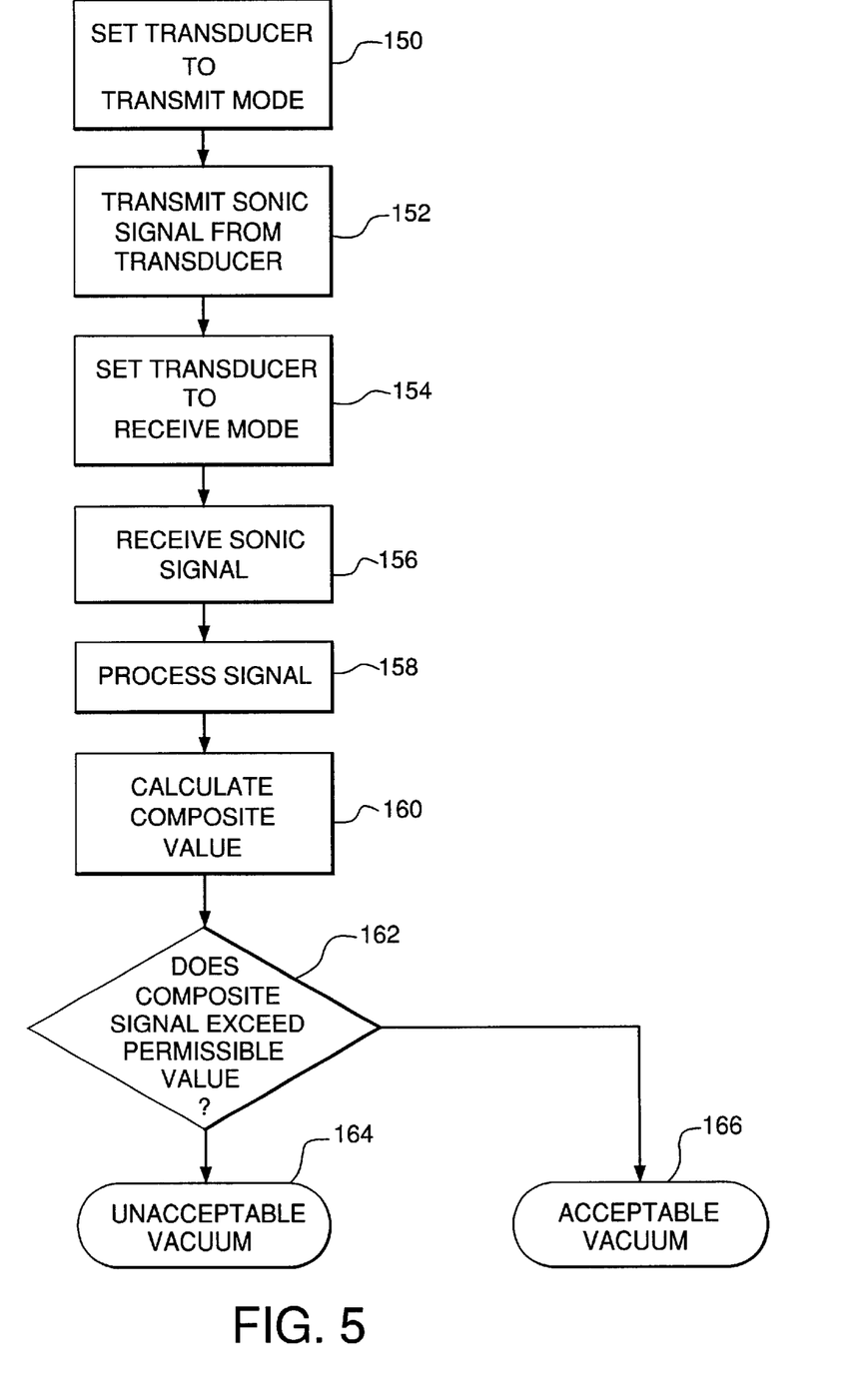
FIG. 5 is a flow chart of a method for monitoring the integrity of a vacuum in accordance with another aspect of the present invention.

FIG. 5 is a flow chart of an alternative method of monitoring vacuum integrity. This alternative method presumes that a single transducer is used both to send and receive sonic signals. At step 150, the transducer is set to transmit. At step 152, a sonic signal is sent from the transducer. At step 154, the transducer is set to receive reflected signals. At step 156, the sonic signal is received at the transducer. Steps 150 through 156 are repeated to accumulate multiple measurements of reflected signals. At step 158, the reflected signals are processed in order to prepare the signal for further consideration. For example, with respect to the signals depicted in FIG. 2, it might be useful to filter the signal received during time T1 so that only those values received during time T2, i.e. those that are more clearly definitive, are considered. At step 160, a composite signal is calculated from the reflected signals. At step 162, it is determined whether the composite signal exceeds a predetermined permissible value. If so, at step 164, it is determined that the vacuum is unacceptable. If the composite is less than the predetermine value, at step 166, it is determined that the vacuum is acceptable.

Figure 6:
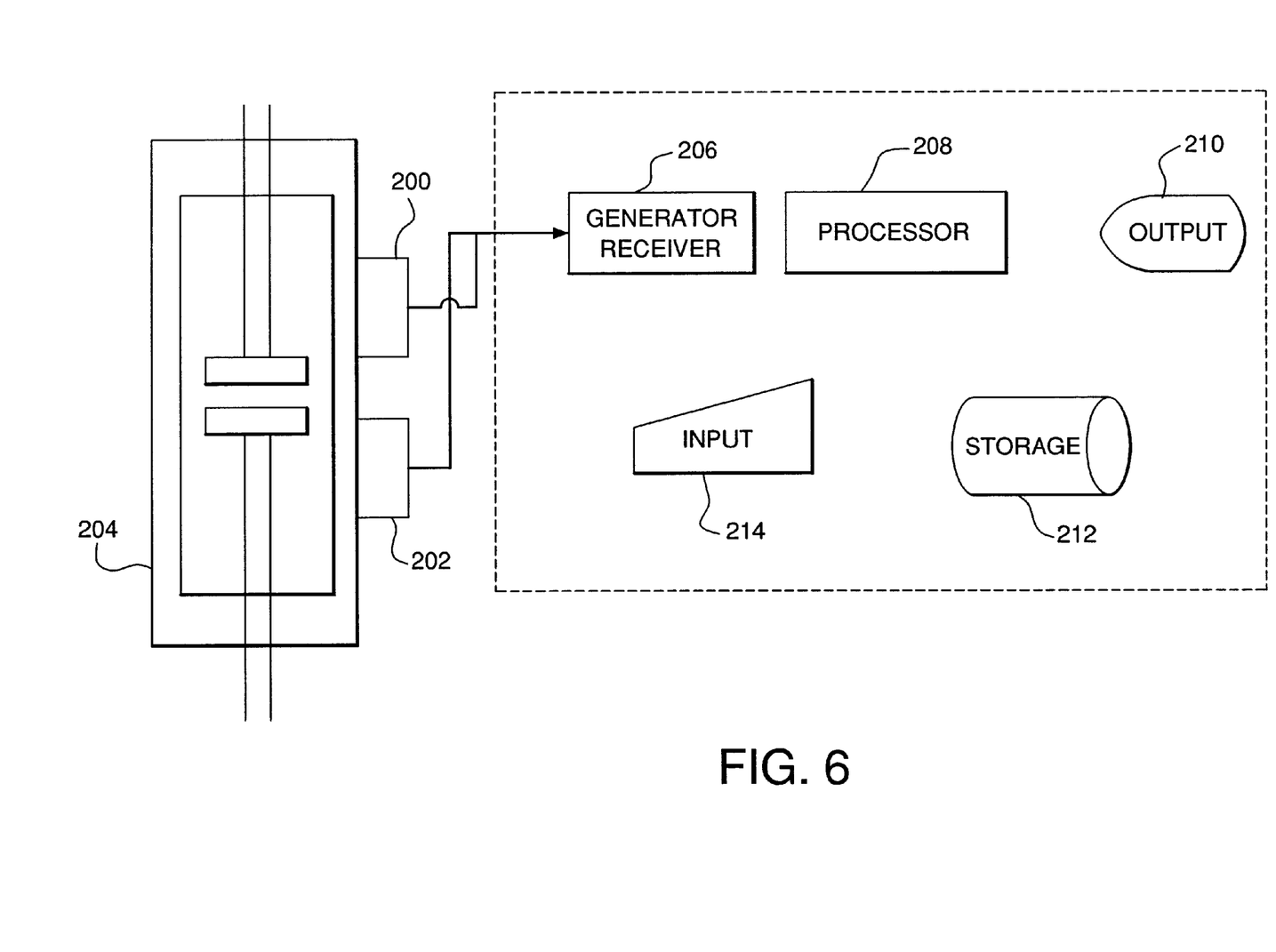
FIG. 6 is a block diagram of a system in accordance with the present invention.

FIG. 6 is a block diagram of a system in accordance with the present invention for performing the above described methods. As shown, transducers 200 and 202, which may be one of many such devices well known to those skilled in the art, are adjacent to vacuum interrupter 204. Signal generator/receiver 206 is connected to both transducers 200 and 202. An electrical signal is generated at generator/receiver 206 and converted to a sonic signal, preferably ultrasonic, at transducer 200. At least a portion of the ultrasonic signal is reflected from interrupter 204 and converted to an electrical signal at transducer 202. The electrical signal is transmitted from generator/receiver 206 to signal processor 208. Signal processor 208 filters the reflected signal to remove the signal component which is reflected from the transducer envelope. Signal processor 208 compares the resulting filtered signal with a predetermined value to decide whether the signal is indicative of an acceptable vacuum. If processor 208 determines that the filtered signal is acceptable, an indication of such is made at output device 210. If processor 208 determines that the filtered signal is unacceptable, an indication to that effect is made at output device 210. Output device 210 may be a CRT display, a series of LED's, or any other visual output device. Output device 210 might also include audio output devices such as speakers. Signal processor 208 is also electrically connected to a data storage device 212. Data storage device 212 might be a disk drive and/or RAM and can be used to store any reference signals such as the predetermined value referred to above. Data storage device 212 might also be employed to store the signals that are received. The system might further include user input device 214, such as a keyboard, pointing device, and/or voice recognition unit, from which a user can control operation of the system.

Figure 7:
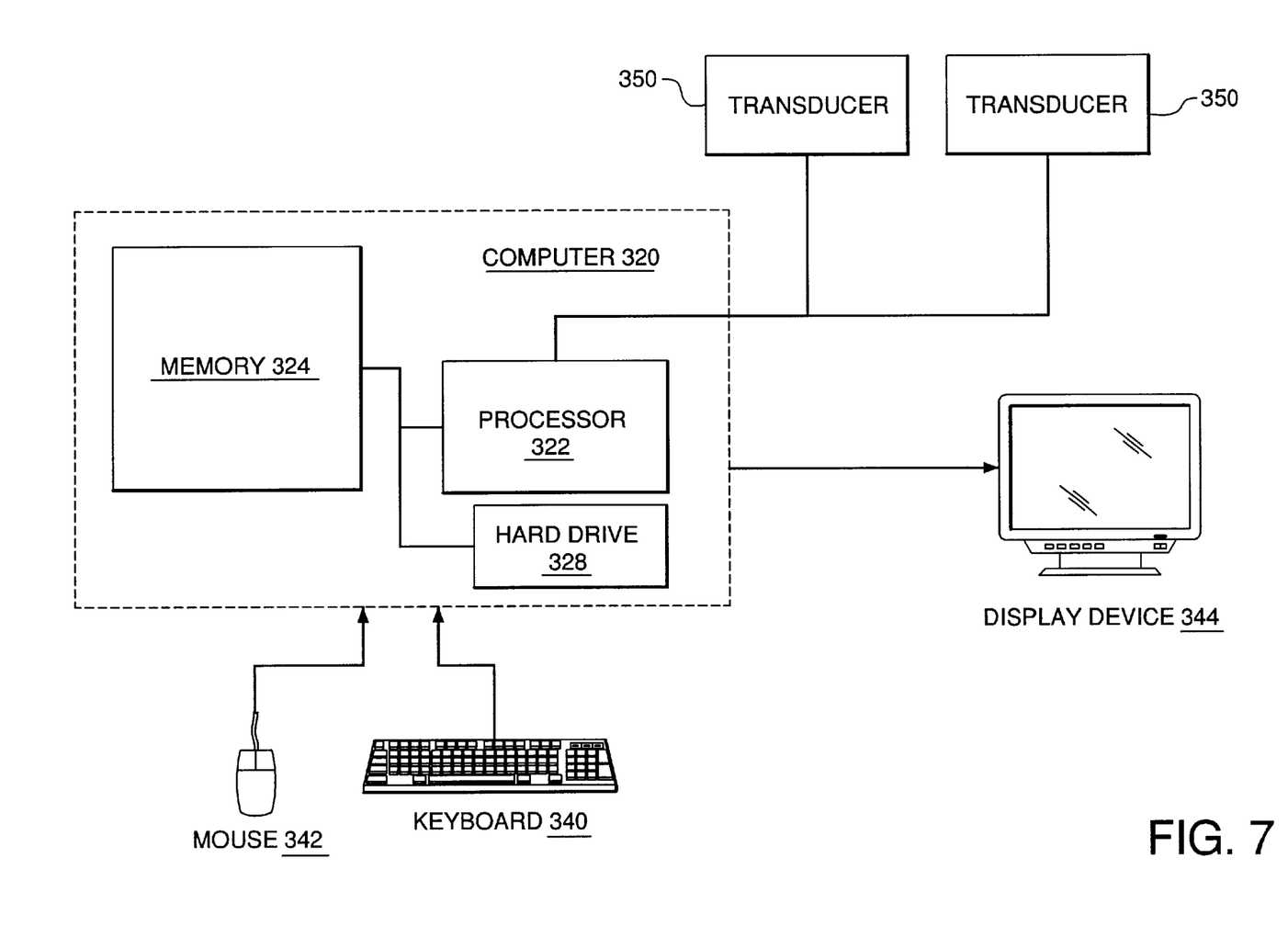
FIG. 7 is a block diagram of a computing device which may be programmed to operate in accordance with the present invention.

It should also be noted that the remaining system components might be embodied in a general purpose computing device. For example, a computing system such as that depicted in FIG. 7 is easily adaptable to embody each of the above described system components. As shown in FIG. 7, computing device 320 includes processing unit 322, system memory 324, and system bus 326 that couples various system components including system memory 324 to the processing unit 322. The system memory might include read-only memory (ROM) and random access memory (RAM). The system might further include hard-drive 328 which provides storage for computer readable instructions, data structures, program modules and other data. A user may enter commands and information into the computer 320 through input devices such as a keyboard 340 and pointing device 342. A monitor 344 or other type of display device is also connected to the system for output.

Processor 322 is connected to transducers 350 and can be programmed with instructions to interact with transducers 350 so as to perform the algorithms described above with reference to FIGS. 3 and 4. The instructions may be stored in memory 324 and/or hard drive 326. Thus, processor 322 may generate and receive signals, filter unnecessary signals, compute a composite value, and compare the composite value with a predetermined value to determine whether an acceptable vacuum has been found.

While the invention has been described and illustrated with reference to specific embodiments, those skilled in the art will recognize that modification and variations may be made without departing from the principles of the invention as described above and set forth in the following claims. In particular, the present invention has been explained with reference to an exemplary computing device but may be employed in other devices. The computing device will likely be a mobile computing device. Also, one or more of the system components described above may be embodied in a single physical device. Accordingly, reference should be made to the appended claims as indicating the scope of the invention.

What is claimed is:

1. A system for vacuum integrity monitoring in a body comprising:
    a transducer for sending sonic signals into the body;
    a receiver for receiving sonic signals reflected from the body;
    a signal processor for calculating a composite value from the sonic signals reflected from the body, said composite value being derived from the sonic signals reflected from the body over a prescribed period of time; and
    a processing unit for determining from said composite value whether the body has an acceptable vacuum therein.

2. The system of claim 1, wherein said composite value is an average.

3. The system of claim 2, wherein said processing unit determines that an acceptable vacuum exists in the body if the composite value is equal to or less than a predefined value.

4. The system of claim 1, wherein said signal processor filters sonic signals reflected from the body that are detected prior to a predefined time from when signals are injected into the body.

5. The system of claim 1 wherein said signal processor calculates the composite value from the sonic signals reflected from the body and received after a predetermined time from when signals are first injected into the body.

6. The system of claim 1 further comprising a display unit for displaying the signals received by said receiver.

7. The system of claim 1 further comprising an output device to indicate if a vacuum has been found to be acceptable.

8. The system of claim 7, wherein said output device is an optical output.

9. The system of claim 7 wherein said output device comprises an LED.

10. The system of claim 7 wherein said output device is an audio output device.

11. The system of claim 3 further comprising a database for storing said predefined value.

12. The system of claim 11 wherein said database stores the sonic signals received at said receiver.

13. The system of claim 1 wherein the sonic signals are ultrasonic signals.

14. A method for vacuum integrity sensing in a body, comprising the following acts:
    injecting sonic signals into the body;
    detecting sonic signals reflected from the body;
    calculating a composite value from the sonic signals reflected from the body, said composite value being derived from the sonic signals reflected from the body over a prescribed period of time; and
    determining using said composite value if the body has an acceptable vacuum therein.

15. The method of claim 14, wherein said act of determining using said composite value if the body has an acceptable vacuum therein, further comprises the acts of,
    if the composite value is greater than a predefined value, identifying the body as having an unacceptable vacuum; and
    if the composite value is less than a predefined value, identifying the body as having an acceptable vacuum.

16. The method of claim 14, further comprising the act of filtering the sonic signals reflected from the body that are detected prior to a predefined time from the commencement of the act of injecting sonic signals.

17. The method of claim 14, wherein said act of determining using said composite if the body has an acceptable vacuum therein, further comprises the act of, if the composite value is equal to a predefined value, identifying the body as having an acceptable vacuum.

18. The method of claim 14, wherein the act of calculating a composite value from the sonic signals reflected from the body is performed using sonic signals reflected from the body that are detected after a predefined time from the commencement of the act of injecting sonic signals.

19. The method of claim 14, further comprising the act of generating an output to identify that the vacuum is acceptable.

20. The method of claim 19, wherein the act of generating an output comprises creating a message on a video display.

21. The method of claim 19, wherein the act of generating an output comprises illuminating a light emitting device.

22. The method of claim 19, wherein the act of generating an output comprises generating an audio signal.

23. In a vacuum system comprising a transducer having a send mode and a receive mode, and a signal processing unit, a method for sensing vacuum integrity in a body, comprising the following acts:
    setting the transducer to the send mode;
    injecting a sonic signal into the body with the transducer;
    setting the transducer to a receive mode;
    receiving a sonic signal at the transducer;
    calculating a composite value from the sonic signals reflected from the body, said composite value being derived from the sonic signals reflected from the body over a prescribed period of time; and
    determining using said composite value if the body has an acceptable vacuum therein.

* * * * *